United States Patent
Hoheisel et al.

(10) Patent No.: US 6,208,708 B1
(45) Date of Patent: Mar. 27, 2001

(54) X-RAY MAMMOGRAPHY APPARATUS HAVING A SOLID-STATE RADIATION DETECTOR

(75) Inventors: Martin Hoheisel, Erlangen; Juergen Kirsch, Oberpframmern; Hartmut Sklebitz; Martin Spahn, both of Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/338,900

(22) Filed: Jun. 23, 1999

(30) Foreign Application Priority Data

Jun. 23, 1998 (DE) .............................................. 198 27 964

(51) Int. Cl.⁷ ...................................................... A61B 6/04
(52) U.S. Cl. ...................... 378/37; 378/98.8; 250/370.09
(58) Field of Search ............... 378/37, 98.8; 250/370.09, 250/370.08, 370.14

(56) References Cited

U.S. PATENT DOCUMENTS 4,689,487 * 8/1987 Nishiki et al. .
5,105,087 * 4/1992 Jagielinski ....................... 250/370.09
5,773,832 * 6/1998 Sayed et al. ..................... 250/370.09
5,773,839 * 6/1998 Krepel et al. .................... 250/370.09
5,798,558 * 8/1998 Tyson et al. ........................... 257/458
6,072,224 * 6/2000 Tyson et al. ..................... 250/370.08

FOREIGN PATENT DOCUMENTS 0 714 038    5/1996  (EP) .

OTHER PUBLICATIONS

Specification Sheet for Mammomat 3000 Opdima™—Digital Biopsy and Spot Imaging System, Siemens–Elema.

* cited by examiner

Primary Examiner—David P. Porta
Assistant Examiner—Pamela R. Hobden
(74) Attorney, Agent, or Firm—Schiff Hardin & Waite

(57) ABSTRACT

An X-ray mammography device has an X-ray tube arrangement, a compression mechanism, a subject table, and a large-area solid-state detector made of amorphous silicon (a-Si) which is integrated in a detector cassette that can be inserted into the subject table and that has a first part of at least one transmission path for supplying the operating voltage, and/or the control signals for operating the solid-state detector and/or the readout data, this first said part engaging functionally with a corresponding second part of the transmission path which is attached at the subject table.

13 Claims, 4 Drawing Sheets

X-RAY MAMMOGRAPHY APPARATUS HAVING A SOLID-STATE RADIATION DETECTOR

BACKGROUND OF THE INVENTION

1. Field of the Invention

The present invention relates to an X-ray mammography device of the type having an X-ray tube arrangement, a compression device, a subject table and a solid-state radiation detector. X-ray diagnostic means of this type serve to examine the breast of a patient.

2. Description of the Prior Art

X-ray mammography devices that are popular today operate with film-foil systems. These systems do not require a large space since the image sensor does not have to transmit electrical signals to the device.

The Siemens data sheet "MAMMOMAT 3000, OPDIMA—Digital biopsy and spot imaging system," (ref. no. WS 0597 7) teaches an X-ray mammography device in which a CCD image sensor is arranged in a cassette, this image sensor having a small image surface (49×85 mm$^2$) compared to the cassette format (18×24 cm$^2$). This CCD cassette is connected via a cable to a workstation which produces the mammographic X-ray images from the signals supplied by the CCD cassette. Since the CCD image sensor occupies only a small space in the cassette, the necessary electronics can be accommodated in this cassette as well without a problem. The rather small detector surface, however, is disadvantageous because it does not permit large-format examinations such as are known in film technology. If larger areas are to be examined, several exposures are necessary, which means a correspondingly increased radiation load on the examination subject. The cable also has a disruptive effect.

In newer X-ray mammography devices, solid-state image sensors such as a-Si panels are employed. Such panels, however, have relatively thick and in part bulky control and readout electronics arranged at the detector so that such detectors occupy a large volume. In order not to limit the variety of diagnostic methods of image capture, i.e. in order not to limit the acceptance of such devices, the detector surface area is reduced in order to keep the dimensions small.

There are also relatively thick sensor arrays with optical guides which complicate or prevent their application with adipose patients.

The dimensions of conventional solid-state detectors often exceed the length and width of the actual radiosensitive surface to a considerable degree. This is unacceptable for a solid-state mammography detector. Specific measures must therefore be taken which enable the active surface to be expanded to the edge of the cassette to within a millimeter.

SUMMARY OF THE INVENTION

An object of the present invention is to provide a mammography device of the general type initially described which enables an alternating pickup with a film and with a solid-state image converter, and which is compactly constructed such that free and virtually unimpeded access to the examined patient is possible.

The object is inventively achieved in an X-ray mammography apparatus having a large area solid-state detector made of amorphous silicon (aSi) integrated in a detector cassette that can be inserted into the subject table, and that includes a part of at least one transmission path for the supply of the operating voltage, and/or the control signals for operating the solid-state detector and/or the readout data, this transmission path part functionally engaging a second part of the transmission path, which is attached to the subject table.

As used herein, "engage" means that the two transmission path parts mate or communicate or co-operate to allow a signal to proceed between the two transmission path parts.

It has proven advantageous if the solid-state detector is constructed as one unitary piece.

As the transmission path for supplying the operating voltage, the subject table and the detector cassette can be inventively provided with at least-two electrical detachable connections, with an inductive transmitter or with a capacitive transmitter for the operating voltage.

The subject table and the detector cassette can advantageously have an optical, capacitive or inductive transmission path for the control signals for operating the panel.

In an X-ray mammography device with a solid-state detector having a dark reference zone (DNZ) for reducing the quantum noise, in order to expand the active surface to the edge of the cassette to within a millimeter it has proven advantageous to dispose the dark reference zone on the device side of the solid-state detector.

In order to be able to use the space in the detector cassette optimally for the solid-state detector, so that the active surface of the solid-state detector has approximately the same dimensions as the surface area of the cassette, detector electronics can be arranged in a region that is located between the rotary arm of the X-ray device and the detector cassette with the solid-state detector.

In an X-ray mammography device having a motherboard, which carries the detector electronics, connected to the solid-state detector via at least one flexible conductor ribbon, preferably at least one end of the conductor ribbon is provided with a preformed bend, which can be generated by stamping. The width of the housing of the detector cassette thus can be so reduced that the active surface reaches the margin of the cassette, since a space-consuming "natural" bend is not needed.

DESCRIPTION OF THE PREFERRED EMBODIMENTS

Figure 1:
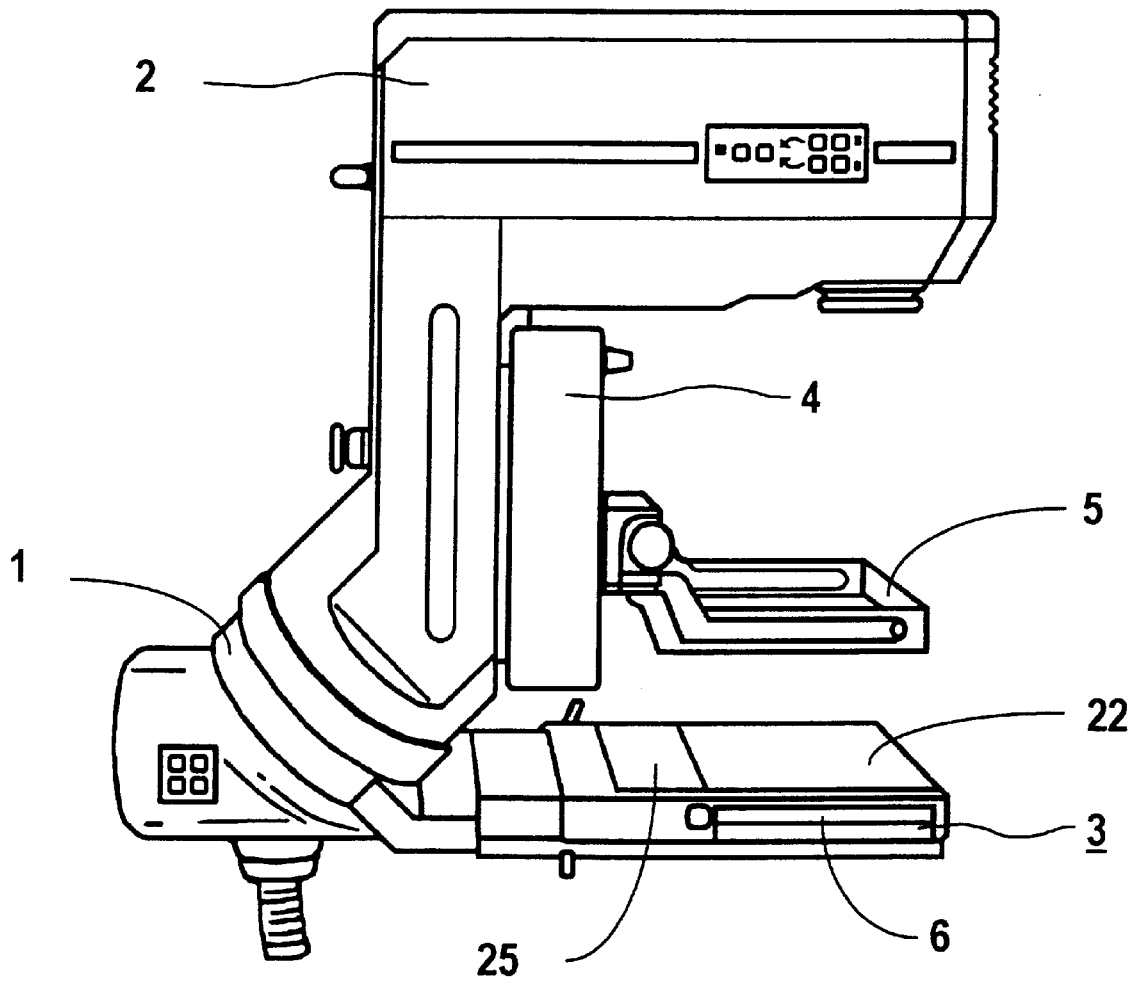
FIG. 1 shows an X-ray mammography apparatus for using an inventive device with a solid-state detector.

FIG. 1 depicts an X-ray mammography device with a rotary arm 1 carrying an X-ray arrangement 2 (with a collimator), a subject table 3 and a compression mechanism 4 with compression plate 5. A detector cassette 6 with a large-area solid-state detector 7, an a-Si semiconductor detector according to the invention, can be inserted into the subject table 3 laterally. This detector has an imaging surface 22.

Figure 2:
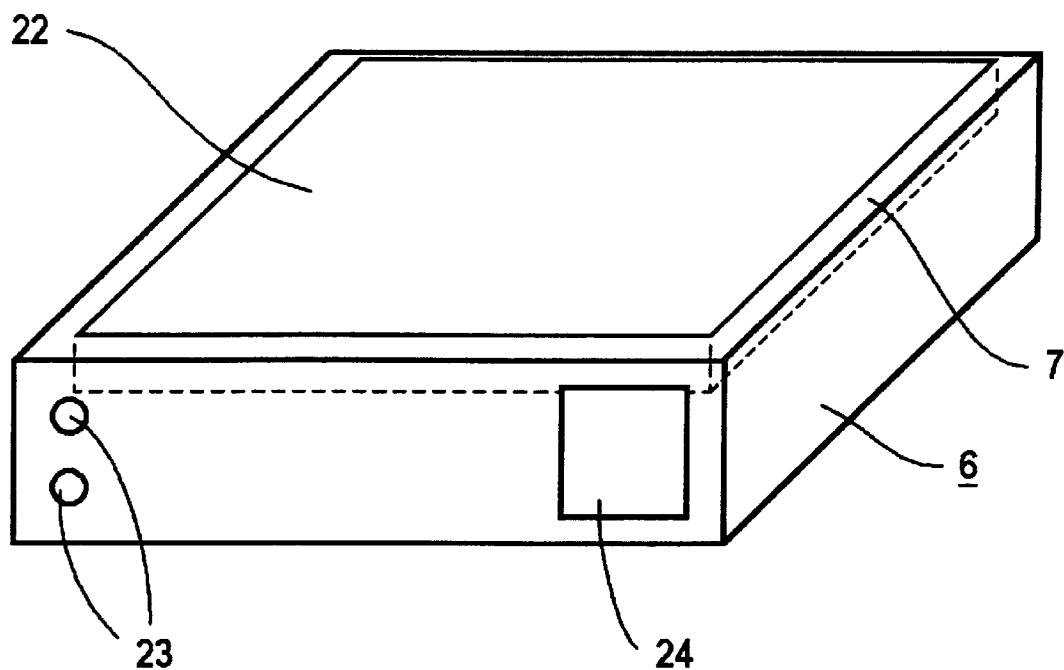
FIG. 2 illustrates an inventive detector cassette for use in the mammography apparatus according to FIG. 1.

The detector cassette 6 with the solid-state detector 7 as illustrated in FIG. 2 is inventively provided with electrical contacts 23 for power supply to the solid-state detector and with a transmitter 24 for the control signals for the operation of the solid-state detector as part of the signal transmitting paths at the cassette side, which functionally engage in corresponding parts that are attached at the subject table 3. The signals for the pickup initiation, different exposure modes, cycles for starting the readout by columns, cycles for readout by rows, and clock signals for resetting the panel subsequent to the readout, or subsequent to the start of an exposure process in the X-ray shot, can be transmitted to this detector cassette 6 optically, capacitively, or inductively. The supply of the operating voltage(s) can also occur inductively or capacitively via additional transmitters (not illustrated).

Figure 3:
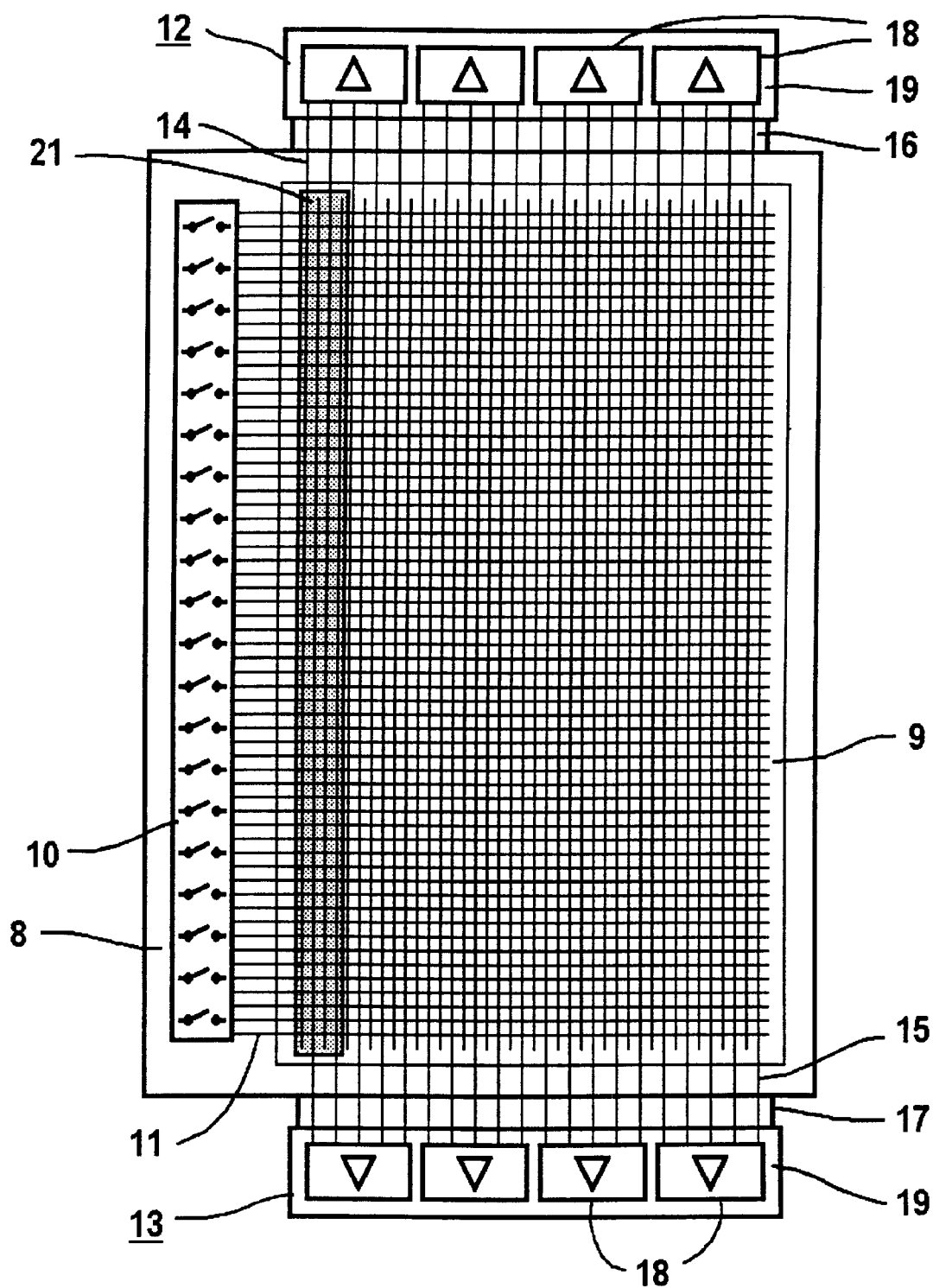
FIG. 3 shows a part of the inventive solid-state detector according to FIG. 2.

FIG. 3 illustrates this solid-state detector, which has a matrix-shaped array 9, the active a-Si photodiode matrix, which is arranged on a glass substrate 8 and which has individual photosensitive cells arranged in n rows and m columns. These cells, in front of which an X-ray converter is arranged, are connected via row lines 11 to control electronics 10 and via column lines 14 and 15 to readout electronics 12 and 13 which are arranged on both sides of the glass substrate 8. The terminals of the readout electronics 12 and 13 are fed to the array 9 at both sides, the column lines 14 and 15 being interleaved, so that the columns are read out first in an upward sequence by the readout electronics 12 and then in a downward sequence by the readout electronic 13, in alternation. These lines can also be arranged such that the column lines 14 and 15 are interrupted in the middle in order to reduce parasitic capacitances, so that the readout electronic 12 captures the entire upper range of pixels, and the readout electronics 13 captures the entire lower range.

The individual photosensitive cells of the active a-Si matrix can each be formed of a photodiode and a switching diode in known fashion, for example, with their cathodes being connected to one another, and their anodes being respectively connected to the row lines 11 or the column lines 14 and 15. Other elements, such as TFTs, can also be used.

The control electronics 10 can be made of polycrystalline silicium placed on the glass substrate 8, while the readout electronics 12 and 13 can be constructed discretely with external electronic modules 18, such as integrated circuits (ICs or ASICs). The electronic modules 18, the readout chips, can contain preamplifier stages and multiplexers.

Figure 4:
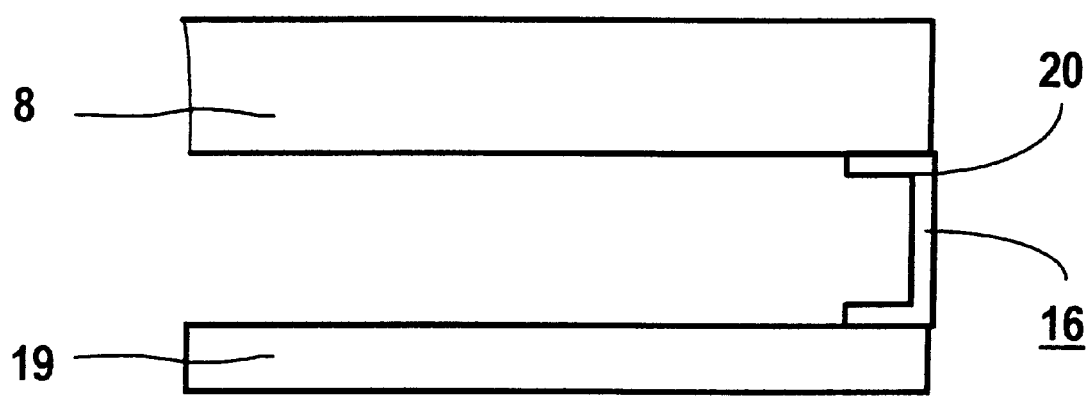
FIG. 4 is a schematic cross-section through the inventive solid-state detector.

The electronic modules 18 are connected to the active a-Si array 9 via connections, e.g. by flexible conductor ribbons 16 and 17. The electronic modules 18 can be attached to one or more motherboards 19 (FIG. 4), which are arranged beneath the glass substrate 8. The flexible conductor ribbons 16 and 17 are inventively provided with angles or bends 20 which are preformed by stamping, for example, so that they do not need to project laterally, or must do so only slightly. Due to these inventive flexible conductor ribbons 16 and 17, it is possible to utilize virtually the entire area of the surface which is provided for the imaging, not only laterally but also in the direction of the examination subject.

The electronic modules 18 are connected via connecting cables (not illustrated) to the other modules of the readout electronics 12 and 13, which can contain amplifier stages and analog/digital converters (A/D converters). These additional modules can be arranged on the same motherboard 19 or on an additional electronic motherboard. These are inventively arranged laterally in a region 25 next to the detector cassette 6 with the solid-state detector 7, in the direction of the rotary arm 1 of the X-ray device. The readout electronics 12 and 13 can also be arranged in this region 25.

German PS 195 27 148 teaches a method for recognizing defects in an a-Si panel, in which method a signal from a dark reference zone (DRZ) is also used for the recognition of defective image points. This dark reference zone is situated at the left image margin, the start of the rows in the radiographic solid-state detector, for example an a-Si detector. It is covered against light and radiation, so that an additional signal does not arise even in a bright image, and it can comprise up to a few hundred columns. The signal values of the unexposed pixels are applied for the correction of the row signal. They serve to reduce the row noise and to correct small transients in the offset. This dark reference zone 21 is inventively arranged on the side of the panel opposite the chest wall, in the direction of the rotary arm 1 of the X-ray device, so that there is not a limitation of the image field at the chest wall.

The inventive detector device exhibits several improvements compared to known a-Si panels, which enable the space-efficient use of a solid-state detector in a known mammography X-ray device. These include the a-Si panel is integrated in an X-ray cassette; this cassette has at least two electrical contacts for supplying the operating voltage(s), for example; the control signals for operating the panel, such as pickup initiation, exposure modes, and clock signals for starting the readout by columns, for the readout by rows and for resetting the panel subsequent to the readout, or for starting an exposure process in the X-ray shot are transmitted to this cassette optically, capacitively, or inductively; the dark reference zone DRZ is arranged on the side of the panel opposite the chest wall; in order not to restrict the diagnostic imaging near the axilla, for example, one or both ends of a conductor ribbon have preformed bend or angle; and in order to avoid limiting the diagnostic methods by keeping the volume requirement low near the patient and particularly by achieving a low thickness of the sensor arrangement, the detector electronics, which is not required directly at the panel, is arranged in the region 25 between the solid-state detector 7 and the rotary arm 1 of the X-ray device.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray mammography apparatus comprising:

an X-ray tube which emits an X-ray beam;

a subject table with a compression arrangement adapted for compressing an examination subject on said subject table in said X-ray beam;

a radiation detector cassette insertable into said subject table, said radiation detector cassette having a large-area solid-state amorphous silicon radiation detector integrated therein, and said detector cassette having a first part of at least one transmission path, said transmission path being selected from the group of transmission paths comprising a transmission path for supplying operating voltage to said solid-state detector, a transmission path for supplying control signals to said solid-state detector for operating said solid-state detector, and a transmission path for reading out data from said solid-state detector; and said subject table having a second part of said transmission path which engages said first part of said transmission path when said detector cassette is inserted into said subject table.

2. An X-ray mammography apparatus as claimed in claim 1 wherein said solid-state detector comprises a single, unitary substrate.

3. An X-ray mammography apparatus as claimed in claim 1 wherein said transmission path comprises said transmission path for supplying an operating voltage to said solid-state detector, and wherein said first part comprises a first electrical connection and wherein said second part comprises a second electrical connection mating with said first electrical connection.

4. An X-ray mammography apparatus as claimed in claim 1 wherein said transmission path comprises said transmission path for supplying an operating voltage to said solid-state detector, and wherein said first part and said second part comprise an inductive transmitter for transmitting said operating voltage from said subject table to said solid-state detector.

5. An X-ray mammography apparatus as claimed in claim 1 wherein said transmission path comprises said transmission path for supplying an operating voltage to said solid-state detector, and wherein said first part and said second part comprise an capacitative transmitter for transmitting said operating voltage from said subject table to said solid-state detector.

6. An X-ray mammography apparatus as claimed in claim 1 wherein said transmission path comprises said transmission path for control signals for operating said solid-state detector, and wherein said first part and said second part comprise a transmitter for said control signals.

7. An X-ray mammography apparatus as claimed in claim 6 wherein said transmitter comprises an optical transmitter.

8. An X-ray mammography apparatus as claimed in claim 1 wherein said transmitter comprises an capacitive transmitter.

9. An X-ray mammography apparatus as claimed in claim 1 wherein said transmitter comprises an inductive transmitter.

10. An X-ray mammography apparatus as claimed in claim 1 wherein said solid-state detector has a side which is closest to said X-ray tube, and wherein said solid-state detector comprises a dark reference zone disposed at said side.

11. An X-ray mammography apparatus as claimed in claim 1 further comprising a rotary arm connecting said X-ray tube and said subject table and further comprising detector electronics, electrically connected to said first part and disposed between said rotary arm and said detector cassette.

12. An X-ray mammography apparatus as claimed in claim 11 wherein said detector electronics include mother board, and further comprising at least one flexible conductor ribbon connecting said mother board to said first part, at least one end of said conductor ribbon having an preformed bend therein.

13. An X-ray mammography apparatus as claimed in claim 12 wherein said preformed bend comprises a preformed bend stamped into said conductor ribbon.

* * * * *